United States Patent [19]

Fariabi

[11] Patent Number: 5,636,641
[45] Date of Patent: Jun. 10, 1997

[54] HIGH STRENGTH MEMBER FOR INTRACORPOREAL USE

[75] Inventor: Sepehr Fariabi, Fremont, Calif.

[73] Assignee: Advanced Cardiovascular Systems, Inc., Santa Clara, Calif.

[21] Appl. No.: 280,209

[22] Filed: Jul. 25, 1994

[51] Int. Cl.$^6$ ............................................. A61B 5/00
[52] U.S. Cl. ........................... 128/772; 623/1; 600/37
[58] Field of Search ........................... 128/657, 772; 604/95, 280, 281, 282, 283; 600/37; 623/1

[56] References Cited

U.S. PATENT DOCUMENTS

| | | | |
|---|---|---|---|
| 4,300,244 | 11/1981 | Bokros | 3/1.4 |
| 4,830,003 | 5/1989 | Wolff et al. | 623/1 |
| 4,917,104 | 4/1990 | Rebell | 128/772 |
| 4,922,927 | 5/1990 | Fine et al. | 128/786 |
| 4,925,445 | 5/1990 | Sakamoto et al. | 128/772 X |
| 5,069,226 | 12/1991 | Yamauchi et al. | 128/772 |
| 5,171,383 | 12/1992 | Sagaye et al. | 128/772 X |
| 5,203,348 | 4/1993 | Dahl et al. | 128/784 |
| 5,213,111 | 5/1993 | Cook et al. | 128/772 |
| 5,230,348 | 7/1993 | Ishibe et al. | 128/772 |
| 5,238,004 | 8/1993 | Sahatjian et al. | 128/772 |
| 5,267,564 | 12/1993 | Barcel et al. | 128/634 |
| 5,282,845 | 2/1994 | Bush et al. | 607/128 |
| 5,303,704 | 4/1994 | Molacek et al. | 128/642 |
| 5,333,625 | 8/1994 | Klein | 128/898 |
| 5,341,818 | 8/1994 | Abrams et al. | 128/772 |
| 5,358,517 | 10/1994 | Pohndorf et al. | 607/116 |
| 5,465,773 | 11/1995 | Hinohara et al. | 128/657 |
| 5,477,864 | 12/1995 | Davisdon | 128/772 |

*Primary Examiner*—Sam Rimell
*Attorney, Agent, or Firm*—Heller Ehrman White & McAuliffe

[57] ABSTRACT

This invention is directed to an intracorporeal device formed of a high strength Co—Ni—Cr alloy and is particularly suitable for forming a composite product with a pseudoelastic member formed of NiTi alloy. Suitable intracorporeal products include guidewires and stents. The high strength alloy consists essentially of about 28 to about 65% cobalt, about 2 to about 40% nickel, about 5 to about 35% chromium, up to about 12% molybdenum, up to about 20% tungsten, up to about 20% iron and the balance inconsequential amounts of impurities and other alloying constituents, with a preferred alloy composition including about 30 to about 45% cobalt, about 25 to about 37% nickel, about 15 to about 25% chromium and about 5 to about 15% molybdenum. Intravascular devices such as guidewires, stents and the like can be formed of this high strength Co—Ni—Cr alloy.

29 Claims, 1 Drawing Sheet

HIGH STRENGTH MEMBER FOR INTRACORPOREAL USE

BACKGROUND OF THE INVENTION

This invention relates to the field of intracorporeal medical devices, and more particularly to elongated intravascular members such as guidewires for percutaneous transluminal coronary angioplasty (PTCA) and stents for maintaining body lumen patency after the body lumen has been dilated with a balloon.

In PTCA procedures a guiding catheter is percutaneously introduced into the cardiovascular system of a patient in a conventional Seldiger technique and advanced therein until the distal tip of the guiding catheter is seated in the ostium of a desired coronary artery. A guidewire is positioned within an inner lumen of a dilatation catheter and then both the catheter and guidewire are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon is properly positioned across the lesion. Once in position across the lesion, the balloon is inflated one or more times to a predetermined size with radiopaque liquid to dilate the stenosis. The balloon is then deflated so that blood flow will resume through the dilated artery and the dilatation catheter and the guidewire can be removed therefrom.

Conventional guidewires for angioplasty and other vascular procedures usually comprise an elongated core member with one or more tapered sections near its distal end and a flexible body such as a helical coil disposed about a distal portion of the core member. A shapable member, which may be the distal extremity of the core member or a separate shaping ribbon such as described in U.S. Pat. No. 5,135,503, hereby incorporated into this application by reference, extends through the flexible body and is secured to a rounded plug at the distal end of the flexible body. Torquing means are provided on the proximal end of the core member to rotate, and thereby steer, the guidewire while it is being advanced through a patient's vascular system. The core member is typically formed of stainless steel, although core member formed of pseudoelastic NiTi alloys are described in the literature and have been used to a limited extent in clinical applications.

Further details of guidewires, and devices associated therewith for angioplasty procedures can be found in U.S. Pat. No. 4,516,972 (Samson); U.S. Pat. No. 4,538,622 (Samson et al.); U.S. Pat. No. 4,554,929 (Samson et al.); and copending application Ser. No. 07/994,679 (Abrams et al.) which are incorporated into this application by reference.

Steerable dilatation catheters with fixed, built-in guidewires or guiding members, such as described in U.S. Pat. No. 4,582,181 (now Re 33,166) are frequently used because they have better pushability than over-the-wire dilatation catheters where the guidewires are slidably disposed within the guidewire lumens of the catheters.

A major requirement for guidewires and other guiding members is that they have sufficient column strength to be pushed through a patient's vascular system or other body lumen without kinking. However, they must also be flexible enough to avoid damaging the blood vessel or other body lumen through which they are advanced. Efforts have been made to improve both the strength and flexibility of guidewires in order to make them more suitable for their intended uses, but these two properties can be diametrically opposed to one another in that an increase in one usually involves a decrease in the other. Efforts to combine a separate relatively stiff proximal section with a relatively flexible distal section frequently result in an abrupt transition at the junction of the proximal and distal section due to material differences.

What has been needed and heretofore unavailable is an elongated intravascular body, such as a guidewire, a stent or the like, which exhibits much higher strength coupled with good ductility than materials currently used to form these types of intravascular devices.

SUMMARY OF THE INVENTION

The present invention is directed to a high strength alloy containing cobalt, nickel, and chromium and particularly to a composite product having a portion formed of the high strength cobalt-nickel-chromium alloy and a portion formed of pseudoelastic alloy such as NiTi alloy.

The product of one embodiment of the invention is an elongated member configured for advancement within a body lumen and is formed at least in part, of high strength alloy comprising about 28 to about 65% cobalt, about 2 to about 40% nickel, about 5 to about 35% chromium and up to about 12% molybdenum. Other alloying components include up to about 20% tungsten, up to about 20% iron and up to about 3% manganese. The alloy may also contain inconsequential amounts of other alloying constituents, as well as impurities, typically less than 0.5% each. A presently preferred alloy composition for use in the intracorporeal product consists essentially of about 30 to about 45% cobalt, about 25 to about 37% nickel, about 15 to about 25% chromium and about 5 to about 15% molybdenum. As used herein all references to percent composition are weight percent unless otherwise noted. The high strength alloy has ultimate strengths up to and exceeding 300 ksi.

Preferably, the intracorporeal product is formed by first cold working the high strength alloy at least 40% of its original transverse cross-sectional area in a plurality of cold working stages with the cold worked product being intermediate annealed between cold working stages at a temperature between about 600° and 1200° C. Those alloys containing molydenum are age hardenable after cold working and annealing at a temperature between about 400° and about 700° C. For optimum tensile strength properties the aging is conducted at about 550° to about 680° C., particularly when the high strength alloy is combined with other alloys as described hereinafter.

In another embodiment of the invention, the cobalt-nickel-chromium alloy is formed into a composite structure with a NiTi alloy which contains about 25 to about 47% titanium and the balance nickel and up to 10% of one or more additional alloying elements. Such other alloying elements may be selected from the group consisting of up to 3% each of iron, cobalt, platinum, palladium and chromium and up to about 10% copper and vanadium. This alloy preferably has a stable austenite phase at body temperature (about 37° C.) and exhibits pseudoelasticity with a stressed induced transformation of the austenite phase to a martensite phase at body temperature at a stress level well above about 50 ksi, preferably above 70 ksi and in many cases above about 90 ksi. The stress levels causing the complete stress-induced transformation of the austenite phase to the martensite phase results in a strain in the specimen of at least about 4%, preferably over 5%. The region of phase transformation resulting from stress preferably begins when the specimen has been strained about 1 to 2% at the onset of the phase change from austenite to martensite and extends to about 7 to about 9% strain at the completion of the phase change. The stress and strain referred to herein is measured by tensile testing. Other methods for determining the stress-strain relationship, e.g., applying a bending moment to a cantilevered specimen, provide a different relationship from the relationship determined by tensile testing, because the stresses which occur in the specimen during bending are not as uniform as they are in tensile testing. The rate of change in stress during the phase transformation is considerably less than the rate of change thereof either before or after the stress-induced transformation. The stress level is relatively constant within the transformation period.

To form the elongated pseudoelastic NiTi member, the alloy material is first cold worked in a plurality of stages, preferably by drawing, to effect a size reduction of at least about 30% and up to about 70% or more in the original transverse cross section thereof with intermediate annealing between the cold working stages at temperatures between about 600° to about 800° C. for about 5 to about 30 minutes. After the final cold working stage the cold worked product is given a final anneal at a temperature of about 700° C. to generate final properties. Preferably, the cold worked NiTi alloy product is subjected to tension during the final annealing and/or provided with a mechanical straightening followed by thermal treatment to help develop a straight memory. The ultimate tensile strength of the material is well above 200 ksi with an ultimate elongation at failure of about 15%.

In one aspect of the invention the cobalt-nickel-chromium containing alloy and another alloy such as the NiTi alloy described above are cold worked together into a composite product, with both alloys being subjected to the same thermomechanical processing to develop a desirable combination of properties. In particular, a presently preferred thermomechanical processing includes a plurality of drawing steps with a reduction of at least about 25% in each cold working stage. The cold worked product is intermediate annealed between cold working stages at a temperature of about 600° and 900° C., e.g. about 750° C. with a time at temperature of about 10 to about 15 minutes. The amount of cold work in the last working stage should be at least about 50% and can be as high as 95% or more. However, the actual cold working in the final working stage is usually determined by the elongation or ductility desired in the final product after straightening and aging.

In the above embodiment the elongated Ni—Ti alloy product is an inner member disposed within the inner lumen of an elongated sheath formed of a Co—Ni—Cr—Mo alloy with an appropriate lubricant and then the assembled unit is processed in a series of size reduction steps involving drawing, or other cold working, followed by an intermediate annealing as described above. The annealing may be performed in line with the drawing. The Co—Ni—Cr—Mo alloy sheath and the NiTi alloy inner member should be recrystallization annealed prior to assembly and cold work to provide maximum ductility by maintaining an equiaxed grain structure and minimum grain growth. After the final cold working step, the composite product is heat treated at a temperature between about 500° and 700° C. and preferably between about 550° and 675° C. for about one minute to about four hours to age harden the cladding and provide pseudoelastic characteristics to the inner member. Tension may be applied during the aging treatment to straighten the product while it is being aged and to provide a straight memory to the NiTi alloy portion of the composite. For composite products with an inner member formed of alloys other than Ni—Ti alloys, the aging conditions, i.e. the temperature and the time at temperature, may be different than that described above for NiTi alloys.

In an alternative embodiment, the NiTi alloy product and the Co—Ni—Cr alloy product can be first prepared separately to their desired final properties and then combined together by suitable means to form the composite product. For example, after final processing, the Co—Ni—Cr alloy sheath can be heated to expand the inner lumen therein so that an NiTi inner member can be readily inserted therein. After insertion of the NiTi inner member into the inner lumen of the sheath, the latter can be cooled so that it shrink fits about the NiTi inner member. Alternatively, the NiTi inner member can be inserted into the sheath after processing while the sheath is still at elevated temperatures and then cooled to contract the sheath onto the NiTi inner member. Other means for combining the NiTi product and the Co—Ni—Cr product includes the use of an adhesive bond therebetween or a physical connection such as a set screw extending through the sheath into the core member or some other type of mechanical connection. A wide variety of other means for joining the Ni—Ti product and the Co—Ni—Cr are contemplated and will become apparent to those skilled in the art.

The products of the invention exhibit a very high level of tensile strength, yet they have excellent ductility. The age hardened Co—Ni—Cr—Mo alloy can have ultimate tensile strengths above 300 ksi and the NiTi alloys can have ultimate tensile strengths exceeding 200 ksi. These products are biocompatible and are particularly useful in medical devices, which are to be utilized intracorporeally, such as guidewires, stents and the like. These and other advantages of the invention will become more apparent from the following detailed description of the invention when taken in conjunction with the accompanying exemplary drawings.

DETAILED DESCRIPTION OF THE INVENTION

Figure 1:
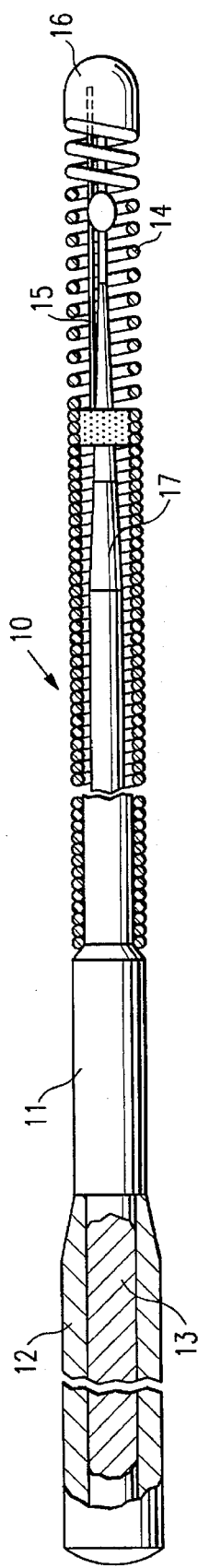
FIG. 1 is an elevational view, partially in section, of a guidewire embodying features of the invention.

FIG. 1 illustrates a guidewire 10 which includes a core member 11 having an outer sheath 12 formed of a Co—Ni—Cr alloy and an inner member 13 formed of Ni—Ti, a helical coil 14 on the distal end of the core member with a shaping ribbon 15 extending between the distal end of the core member and a rounded plug 16 which connects the distal end of the shaping ribbon with the distal end of the helical coil. The distal section 17 of the core member 11, which is disposed primarily within the coil 14, is tapered to sequentially smaller diameters to provide gradually increasing flexibility along the length of the distal portion of the guidewire 10. The taper is formed by removing the sheath 12 formed of high strength Co—Ni—Cr alloy which exposes the inner NiTi alloy member 13 having moderate strength and substantial flexibility which may then be ground in a conventional manner to one or more smaller diameter sections.

Figure 2:
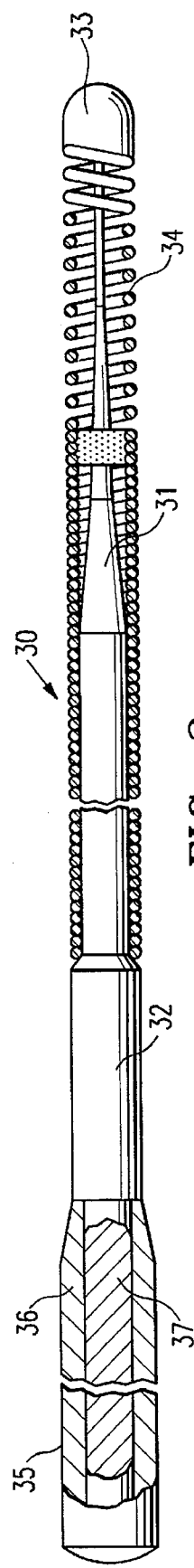
FIG. 2 is an elevational view, partially in section, of an alternative guidewire structure embodying features of the invention.

FIG. 2 depicts a guidewire 30 with a construction wherein the tapered distal section 31 of the core member 32 extends to the plug 33 which connects the distal end of the core member to the distal end of the helical coil 34 disposed about the distal section of the core member. The proximal section 35 of the core member 32 is of composite construction as in the prior embodiment with a sheath 36 of high strength Co—Ni—Cr alloy and an inner member 37 of a pseudoelastic NiTi alloy. The high strength sheath 36 is removed from the core member to form the tapered distal section 31 to increase the flexibility of the distal section of the guidewire 30.

The elongated proximal portions of the guidewires are generally about 130 to about 140 cm in length with an outer diameter of about 0.006 to about 0.018 inch for coronary use. Larger diameter guidewires may be employed in peripheral arteries and other body lumens. The lengths of the smaller diameter and tapered sections can range from about 2 to about 20 cm, depending upon the stiffness or flexibility desired in the final product. The helical coil is about 20 to about 45 cm in length, has an outer diameter about the same size as the diameter of the elongated proximal portion, and is made from wire about 0.002 to about 0.003 inch in diameter. The shaping ribbon and the flattened distal section of distal portion have rectangular transverse cross-sections which usually have dimensions of about 0.001 by 0.003 inch. The overall length of a guidewire is typically about 175 cm.

A presently preferred cobalt-nickel containing alloy is commercially available as MP35N from Carpenter Technology Corporation which has a nominal composition of about 35% cobalt, about 35% nickel, about 20% chromium and about 10% molybdenum. Other commercially available alloys include Elgiloy from Elgiloy Limited Partnership and Haynes 188 from Haynes International.

The following example is given to illustrate the method of forming the core member of a guidewire in accordance with the invention. A NiTi alloy rod having a composition of about 55.9% Ni and 44.1% Ti was drawn to a diameter of about 0.06 inch. The as-drawn wire, which was in a cold worked condition (e.g. 50% cold work), was ground or etched to remove tenaceous surface oxides and then annealed at 700° C. for about one hour. A tubular sheath having a nominal composition of 35% Co, 35% Ni, 20% Cr and 10% Mo was formed with an outer diameter of about 0.114 inch and an inner diameter of about 0.068 inch in an annealed condition. The NiTi wire was disposed within the inner lumen of the high strength sheath and the assembly was drawn in a series of five stages with a 50% reduction in area followed by heat treating at 750° C. for 15 minutes in each stage. The fifth stage was followed by a sixth stage which included drawing with a cold work of about 16% followed by heat treating at 750° C. and a seventh stage which included drawing with a cold work of about 50% but with no heat treating. The final cold worked product was aged at temperatures of about 650° for about one minute to develop maximum bending, yield and modulus with minimum spring back.

The composite core member of the invention provides a number of favorable properties and characteristics. The outer sheath of high strength cobalt-nickel alloy provides the necessary stiffness and push and the inner NiTi alloy member provides the desirable distal flexibility. Another advantage of the composite product of the present invention, when utilized as a core member of a guidewire, is that the proximal end of the flexible coil can be soldered or brazed to the Co—Ni—Cr alloy sheath so as to avoid the problems with soldering the coil to a NiTi alloy which is very difficult to bond to by conventional soldering techniques because of the tenaceous oxide which usually forms on the surfaces of titanium containing alloys.

Figure 4:
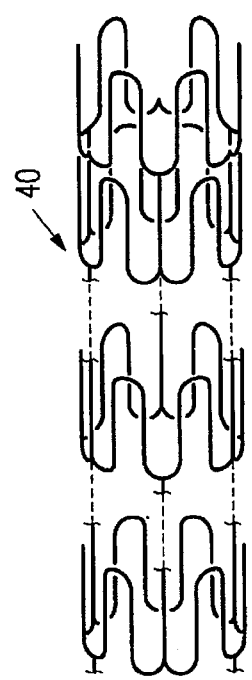
FIG. 4 is a perspective view of an intravascular stent which may be formed of the alloy composition of the invention.
Figure 3:
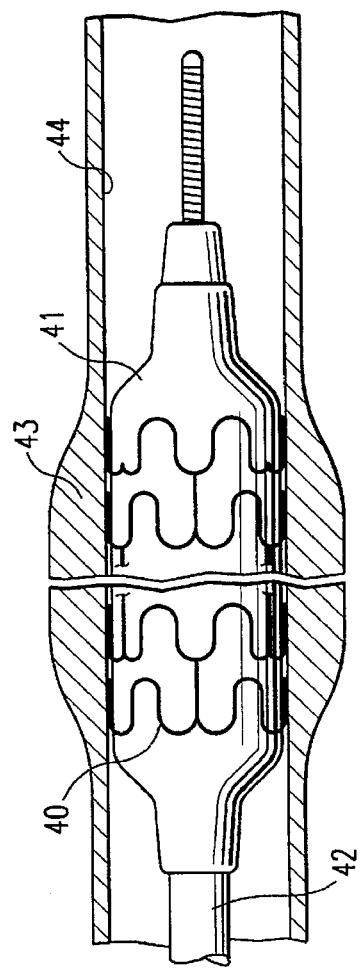
FIG. 3 is an elevational view, partially in section of a stent being expanded by an inflatable balloon on an intravascular catheter within a stenosed region of a patient's artery.

FIGS. 3 and 4 illustrate another embodiment of the invention wherein the high strength Co—Ni—Cr alloy is in the form of an intraluminal stent 40, which as shown in FIG. 3, is expanded by the balloon 41 of catheter 42 within a stenosis 43. After permanent expansion of the stent 40 within the body lumen 44, such as a coronary artery, the balloon 41 is deflated and the catheter 42 withdrawn. The high strength developed by the Co—Ni—Cr alloy allows the stent to be formed of thinner material, yet provide the radial rigidity to hold the body lumen upon deflation of the balloon. The balloon utilized to expand the stent is similar in many respects to a dilatation balloon used in angioplasty procedures in that it is a generally inelastic balloon formed of a suitable polymeric material such as a high density polyethylene, polyethylene terephthalate and polyolefin, e.g. Surlyn®. A particularly suitable stent design is disclosed in copending application Ser. No. 08/164,986, filed on Dec. 9, 1993 which is assigned to the present assignee and which is incorporated herein by reference.

While the present invention has been described herein in terms of certain preferred embodiments, those skilled in the art will recognize that a variety of modifications and improvements can be made to the present invention without departing from the scope thereof.

What is claimed is:

1. An elongated member configured for advancement within a body lumen which is formed at least in part of a cold worked biocompatible alloy consisting essentially of 28 to 65% by wt. cobalt, 2 to 40% by wt. nickel, 5 to 35% by wt. chromium, up to 12% by wt. molybdenum, up to 20% by wt. tungsten and up to 20% by wt. iron.

2. The elongated member of claim 1 wherein the cold worked biocompatible alloy includes 30 to 45% by wt. cobalt, 25 to 37% by wt. nickel, and 25% by wt. chromium and 5 to 15% by wt. molybdenum.

3. The elongated member of claim 2 wherein the cold worked biocompatible alloy has been age hardened.

4. The elongated member of claim 1 in the form of a guidewire.

5. The elongated member of claim 1 wherein a distal portion thereof is formed of a pseudoelastic NiTi alloy.

6. A composite product comprising:
   a) a first portion formed of a high strength alloy containing 28 to 65% by wt. cobalt, 2 to 40% by wt. nickel and 5 to 35% by wt. chromium; and
   b) a second portion formed of an alloy of nickel and titanium.

7. The composite product of claim 6 wherein the second portion exhibits a stress induced transformation from an austenite phase which is stable at body temperature to a martensite phase.

8. The composite product of claim 6 having an elongated shape with the second portion being an elongated inner member and the first portion being an outer sheath disposed about the inner member.

9. The composite product of claim 8 wherein the composite product has proximal and distal sections and has at least a portion of the outer sheath removed from the inner member in at least part of the distal section.

10. The composite product of claim 9 wherein the inner member in the distal section tapers in the distal direction to a smaller transverse dimension.

11. A co-worked high strength elongated composite intracorporeal device comprising:
    a) a first member formed of a pseudoelastic NiTi alloy which has; desirable mechanical properties due to having been subjected to certain thermomechanical processing; and
    b) a second member secured to the first member formed of a high strength alloy which contains 28 to 65% by wt. cobalt, 2 to 40% by wt. nickel and 5 to 35% by wt. chromium and which has been subjected to the same thermomechanical processing to which the first member has been subjected.

12. The intracorporeal device of claim 11 wherein the thermomechanical processing includes a plurality of cold working stages with intermediate anneals and a final cold working stage followed by an age hardening heat treatment.

13. An elongated guidewire for intracorporeal use comprising:
    a) a core member having
        an inner portion formed of a pseudoelastic NiTi alloy; and
        an outer portion formed of a high strength alloy which contains 28 to 65% by wt. cobalt, 2 to 40% by wt. nickel and 5 to 35% by wt. chromium; and
    b) a helical coil disposed about a distal portion of the core member.

14. The elongated guidewire of claim 13 having proximal and distal sections with a length of the outer portion removed to expose the underlying inner portion in the distal section of the guidewire.

15. The elongated guidewire of claim 14 wherein the helical coil is disposed about the exposed portion of the core member.

16. The elongated guidewire of claim 15 wherein the helical coil is secured by its proximal portion to the outer portion of the core member.

17. The elongated guidewire of claim 16 wherein a shapeable ribbon having proximal and distal ends is secured by its distal end to the distal end of the coil and by its proximal end to the core member.

18. The elongated guidewire of claim 16 wherein the helical coil is secured by its distal end to the core member.

19. The elongated guidewire of claim 13 wherein the Co—Ni—Cr alloy consists essentially of 28 to 65% by wt. cobalt, 2 to 40% by wt. nickel, and 5% to 35% by wt. chromium and up to 12% by wt. molybdenum, up to 20% by wt. tungsten, up to 20% by wt. iron and the balance inconsequential amounts of other alloying constituents and impurities.

20. The elongated guidewire of claim 19 wherein the Co—Ni—Cr alloy includes 30 to 45% by wt. cobalt, 25 to 37% by wt. nickel, 15 to 25% by wt. chromium and about 5 to about 15% by wt. molybdenum.

21. The elongated guidewire of claim 13 wherein the Ni—Ti alloy consists essentially of 25 to 47% by wt. titanium and the balance nickel and up to about 10% by wt. of one or more additional alloying elements.

22. The elongated guidewire of claim 21 wherein the additional alloying elements are selected from the group consisting of up to 3% by wt. of iron, cobalt, chromium, platinum and palladium and up to about 10% by wt. copper and vanadium.

23. A method of making an elongated composite product comprising:
    a) providing an elongated outer sheath formed of a Co—Ni—Cr alloy with an inner lumen extending therein;
    b) advancing an elongated core member formed of NiTi alloy into the inner lumen of the outer sheath to form an assembly therewith; and
    c) cold working the assembly in a plurality of cold working stages and intermediate annealing the cold worked assembly between cold working stages.

24. The method of claim 23 wherein the outer sheath is formed of an alloy containing up to 10% molybdenum.

25. The method of claim 23 wherein the assembly is cold worked by drawing with a reduction of at least about 20% in each cold working stage.

26. The method of claim 23 wherein the cold worked assembly is intermediate annealed at a temperature of about 600° and 900° C.

27. The method of claim 25 wherein the final cold working stage includes a reduction of at least 50%.

28. The method of claim 24 wherein the cold worked assembly is heat treated after the final cold working stage at a temperature between about 400° and about 700° C. to age harden the outer sheath formed of Co—Ni—Cr—Mo alloy and provide pseudoelastic characteristics to the inner member.

29. The method of claim 24 wherein the cold worked assembly is heat treated at a temperature between about 550° and about 675° C. to age harden the outer sheath formed of Co—Ni—Cr—Mo alloy and provide pseudoelastic characteristics to the inner member.

* * * * *